United States Patent
Price et al.

(10) Patent No.: US 6,465,215 B1
(45) Date of Patent: Oct. 15, 2002

(54) IDENTIFICATION OF CELLS FOR TRANSPLANTATION

(75) Inventors: Jack Price; Dafe Uwanogho, both of London (GB)

(73) Assignee: Reneuron Limited, London (GB)

(*) Notice: Subject to any disclaimer, the term of this patent is extended or adjusted under 35 U.S.C. 154(b) by 0 days.

(21) Appl. No.: 09/696,569

(22) Filed: Oct. 25, 2000

Related U.S. Application Data

(60) Provisional application No. 60/170,692, filed on Dec. 14, 1999.

(51) Int. Cl.[7] .......................... C12P 21/06; C12P 19/34; C12Q 1/68
(52) U.S. Cl. .......................... 435/69.1; 435/6; 435/91.2
(58) Field of Search .......................... 435/69.1, 91.2, 435/368, 6

(56) References Cited

U.S. PATENT DOCUMENTS

| | | | |
|---|---|---|---|
| 5,753,491 A | 5/1998 | Major et al. | |
| 5,851,832 A | 12/1998 | Weiss et al. | |
| 5,958,767 A | 9/1999 | Snyder et al. | |

FOREIGN PATENT DOCUMENTS

| | | | |
|---|---|---|---|
| WO | 8903872 | | 5/1989 |
| WO | 9109936 | | 7/1991 |
| WO | 9301275 | | 1/1993 |
| WO | 9615226 | | 5/1996 |
| WO | 9710329 | | 9/1996 |
| WO | WO-97/10329 | * | 3/1997 |
| WO | 9829565 | | 12/1997 |
| WO | 9915700 | | 9/1998 |
| WO | 9927076 | | 11/1998 |
| WO | 9946385 | | 3/1999 |

OTHER PUBLICATIONS

Utans U et al. Chronic cardiac rejection: Identification of five upregulated genes in transplanted hearts by differential mRNA display. Proc.Natl.Acad.Sci.USA., 91: 6463–6467, 1994.*
Gotz M et al. Pax6 controls radial glia differentiation in the cerebral cortex. Neuron, 21:1031–1044, 1998.*
Marra M et al. vi78b11.x1 stratagene mouse testis (3937308) Mus musculus cDNA clone. Accession No. AI507135. EST database search report, Mar. 11, 1999.*
U.S. application No. 09/663,537, Jat, filed Sep. 15, 2000.
U.S. application No. 09/537,617, Hodges, filed Mar. 29, 2000.
U.S. application No. 09/672,606, Sinden et al., filed Sep. 28, 2000.
U.S. application No. 09/760,274, Sinden et al., filed Jan. 12, 2001.
Snyder, Evan Y., David L. Deitcher, Christopher Walsh, Susan Arnold–Aldea, Erika A. Hartwieg, Constance L. Cepko (Jan. 10, 1992) "Multipotent Neural Cell Lines Can Engraft and Particpate in Development of Mouse Cerebellum" *Cell* 68:33–51.

Snyder, Evan Y. and John H. Wolfe (1996) "Central nervous system cell transplantation: a novel therapy for storage diseases?" *Curr. Opin. Neurol.* 9:126–136.
Snyder, Evan Y., Cliff Yoon, Jonathan D. Flax, Jeffrey D. Macklis (Oct. 14, 1997) "Multipotent neural precursors can differentiate toward replacement of neurons undergoing targeted apoptotic degeneration in adult mouse neocortex" *Proc. Natl. Acad. Sci.* 94(21):11663–11668.
Utans, Ulrike, Peng Liang, Lauri R. Wyner et al. (Jul. 1994) "Chronic cardiac rejection: Identification of five upregulated genes in transplanted hearts by differential mRNA display" *Proc. Natl. Acad. Sci. USA* 91:6463–6467.
Götz, Magdalena, Anastassia Stoykova, Peter Gruss (Nov. 1998) "Pax6 Controls Radial Glia Differentiation in the Cerebral Cortex" *Neuron* 21:1031–1044.
Sinden, J.D., F. Rashid–Doubell, T.R. Kershaw, et al. (1997) "Recovery of Spatial Learning By Grafts Of A Conditionally Immortalized Hippocampal Neuroepithelial Cell Line Into The Ischaemia–Lesioned Hippocampus" *Neuroscience* vol. 81 (3):599–608.
Fernandez, Anibal Smith, Claude Pieau, Jacques Repérant et al. (1998) "Expression of the Emx–1 and Dlx–1 homeobox genes define three molecularly distinct domains in the telencephalon of mouse, chick, turtle and frog embryos: implications for the evolution of telencephalic subdivisions in amniotes" *Development* 125:2099–2111.
Puelles, Luis and John L.R. Rubenstein (1993) "Expression patterns of homeobox and other putative regulatory genes in the embryonic mouse forebrain suggest a neuromeric organization" *TINS* 16(11):472–479.
McKay et al. (1990) "Mechanisms regulating Cell Number and Type in the Mammalian Central Nervous System" Cold Spring Harbor Symposia on Quantitative Biology, vol. 55, pp. 291–301.
McKay et al. (1993) "Immortalized Stem Cells Form the Central Nervous System" C.R. Acad. Sci. Pars, Sciences De La Vie, vol. 316, pp. 1452–1457.
Okabe et al. (1996) "Development of Neuronal Precursor Cells and Functional Postmitotic Neurons from Embryonic Stem Cells In Vitro" Mechanisms of Development, vol. 59, pp. 89–102.
Sanberg et al. (Feb., 1998) Proceedings of the 1998 Miami Biotechnology Symposium, vol. 38, pp. 139–142.
Scheffler et al. (1999) *Trends in Neuroscience* vol. 22, pp. 348–357.
Hodges et al. (1997) *Pharm. Biochem. and Behavior* vol. 56, pp. 763–780.
Netto et al. (1993) *Behavioral Brain Res.* vol. 58, pp. 107–112.
Rashid–Doubell et al. (1994) *Gene Therapy* vol. 1, Suppl. 1, p. S63.

* cited by examiner

*Primary Examiner*—Jeffrey Fredman

(57) ABSTRACT

Pluripotent cells that are suitable for transplantation therapy, to repair neural damage, are identified, e.g. by differential display, from a gene expression profile for a selected cell, which can be compared with that obtained from a control cell.

17 Claims, No Drawings

IDENTIFICATION OF CELLS FOR TRANSPLANTATION

CROSS REFERENCE TO A RELATED APPLICATION

This application claims priority to provisional patent Application Ser. No. 60/170,692, filed Dec. 14, 1999.

FIELD OF THE INVENTION

This invention relates to the identification of cells suitable for transplantation into a vertebrate brain. More particularly, this invention relates to the identification of multipotent neural cells which are able to repair neural damage following transplantation into the brain.

BACKGROUND TO THE INVENTION

There is an increasing awareness that damage to a vertebrate brain can be repaired using cell transplantation technology. Typically, the cell transplanted into a damaged brain will be a neural stem cell, e.g. a pluripotent neuroepithelial stem cell which is capable of differentiating into a cell with a neural cell phenotype.

For example, Sinden et al., Neuroscience (1997) 81:599–608, discloses that conditionally-immortalised hippocampus neuroepithelial stem cells can be used to improve spatial learning after transplantation into the ischaemia-leisoned hippocampus. See also WO-A-97/10329.

However, it has been found that not all neural stem cells can be transplanted for successful repair of neural damage.

For example, while MHP36 cells (Sinden et al., supra) do aid repair, an apparently similar cell line, MHP15, fails to repair. This difference emerges despite the fact that both MHP cell lines were generated from the same tissue source (namely hippocampus), and both are multipotent neural precursor cell lines, i.e. both cell lines have the capacity to generate a full complement of brain cell types, including neurons, astrocytes and oligodendrocytes.

Therefore, it would be beneficial if it were possible to identify at an early state, the cells that were suitable for transplantation, or to have the ability to modify cell lines in order to achieve successful transplantation and repair.

SUMMARY OF THE INVENTION

The present invention is based on the realisation that cells that are suitable for transplantation and repair may be identified on the basis of their gene expression profile.

The present invention employs, for example, a technique termed differential display (DD) to investigate the differences between repairing and non-repairing cell lines. Differential display is used to visualise the differences in gene expression between two or more cell lines, and it has been found that cell lines that repair have very similar profiles of gene expression but very different profiles from those cells that do not repair. This represents a major, unexpected discovery because, apart from their capacity to repair, the cell lines are usually remarkably similar, in morphology, growth characteristics and growth factor responsivity.

According to one aspect of the present invention, a method for selecting a cell suitable for transplantation into a damaged vertebrate brain comprises:

(i) isolating cells that are, or are capable of differentiating into, a cell with a neural cell phenotype;

(ii) obtaining the gene expression profile of the cells;

(iii) comparing the expression profile of the cells with that from a control cell known to be suitable for transplantation; and (iv) selecting those cells with a similar expression profile to that of the control.

In one embodiment of the invention, the control cell is from the MHP 36 cell line. Step (ii) may be carried out by differential display.

The present invention is not only useful for identifying suitable cells for transplantation, but may be used to identify genes or gene products that may be involved in determining whether or not a neural cell can repair, or not.

According to a further aspect of the present invention, a method for identifying a gene involved in determining whether or not a neural cell can aid repair on transplantation into a damaged brain, comprises:

(i) isolating cells that are, or are capable of differentiating into, a cell with a neural cell phenotype;

(ii) obtaining the gene expression profile of the cells;

(iii) comparing the expression profile of the cells with that from a control cell line known to be suitable for transplantation; and (iv) isolating those genes that are the same (or different) from those expressed by the control.

Using this method, it has been possible to identify a number of genes that are expressed by repairing cell lines but not non-repairing cell lines (and vice versa).

According to a third aspect, a method for selecting a cell suitable for transplantation into a damaged brain, comprises determining the presence of any of the gene sequences identified herein as SEQ ID NOS. 1 to 5.

BRIEF DESCRIPTION OF THE SEQUENCES

SEQ ID NOS. 1–7 are polynucleotide sequences useful according to the subject invention.

DESCRIPTION OF THE INVENTION

The present invention provides a convenient method for identifying cells that may not be used in transplantation and repair in a damaged vertebrate brain. Using differential display techniques, a cell line can be screened against a control, and a suitable cell line selected for further development.

Although other techniques are known for obtaining gene expression profiles, a differential display technique is preferred. In summary, the technique relies on isolating mRNA from a population of cells, and using this to determine the levels of expression of particular genes. This is most often achieved by using reverse transcription to obtain the copy DNA (cDNA), which is co-amplified using specific and semi-quantitative primer sequences. The results are then compared to a control to evaluate differences in gene expression.

Kits for carrying out differential display are available commercially.

The cells used in the method should be capable of differentiating into a cell with a neural cell phenotype, i.e. the differentiated cell should adopt either a neuron, astrocyte or oligodendrocyte phenotype. Preferably, the cells in the undifferentiated state are multi-potent, i.e. they have the capacity to develop into at least two of the neural cell phenotypes above. Multi-potent cells are known, and procedures for obtaining such cells will be apparent to the skilled person.

The differential display technique may be carried out on the cells in the differentiated or undifferentiated state. It is however preferred if the cells are maintained in the undifferentiated state during the technique. Conditions to maintain the cells in the undifferentiated state are known in the art, and include culture methods making use of growth factors, and recombinant DNA techniques to insert, for example, oncogenes or conditionally-inducible oncogenes into the cells.

The present invention provides a convenient way to identify cells that may be used in transplantation and repair in a damaged vertebrate brain. Using the method of the invention, cell lines can be screened against a control, and a suitable cell line selected for further development.

Genes that are differentially expressed in non-repairing cell lines may be identified. Modification of the genes by, for example, site-directed mutagenesis, may be carried out to inactivate the genes to provide further cell lines that may be suitable for transplantation. For example, disruption of the Pax6 or 3R2C genes may be carried out to prepare cells for transplantation. Methods for modifying or inactivating the genes will be apparent to the skilled person.

Modified cell lines, or cell lines identified by the method of the invention as suitable for transplantation, may be used in conventional transplantation methods. For example, Sinden et al, supra, shows the preparation of stem cells for transplantation into the mouse brain.

The present invention encompasses the use of cells according to the invention, in the manufacture of a composition for the treatment of damage to the vertebrate brain. Suitable formulations for delivery of the cells to the brain will be apparent to the skilled person having regard to the nature of the cell for therapeutic use. Appropriate amounts of cells for therapeutic use, in addition to suitable excipients, diluents or carriers, will be apparent to the skilled person based on conventional formulation methods.

The following Example shows a differential display experiment to identify the gene expression profile of the cell lines MHP 36, MHP 15, MHP 3 and SVE 10.

Example

The cell lines were grown at 33° C., in standard MHP medium containing bFGF, in 175 cm³ flasks. Cells were allowed to become 90% confluent before being transferred to 39° C., and cultured for a further seven days in the absence of interferon.

The cells were washed for five minutes with 20 ml of HBSS (Gibco BRL). The cells were lysed by adding 20 ml of Trizol (Life Technologies), and incubating at 37° C. for ten minutes. The lysate was then transferred to a 50 ml Falcon tube (Stardts) and 5 ml of chloroform added The tubes were mixed vigorously for one minute and the phases separated by centrifugation at 4,000rpm for 15 minutes. The upper aqueous phase was transferred to a fresh 50 ml tube and 7 ml of isopropanol added. RNA was precipitated by placing the tubes at −20° C. for 1 hour. The RNA was pelleted by centrifugation at 4,000 rpm for 20 minutes. The pellet was washed in 70% ethanol (made up in DEPC treated water), centrifuged as described above and allowed to air dry at room temperature for ten minutes. The pellet was then resuspended in 439 µl of DEPC-water and transferred to an RNase free Eppendorf tube.

To remove any contaminating DNA from the RNA sample, the following was added to the resuspended RNA solution; $MgCl_2$ to a final concentration of 5 mM; DDT to 100 mM; RNase inhibitor, 500 units, and DNase I, 700 units. The tubes were then incubated at 37° C. for one hour and the RNA purified by the addition of an equal volume of acid phenol/chloroform/isoamyl alcohol (125:24:1) with vortex- ing for one minute and centrifugation at 14,000 rpm (4° C.) for 6 minutes. The upper aqueous phase was transferred to a fresh Eppendorf tube and the phenol/chloroform extraction repeated until the interface became clear. 8 M LiCl was added to the final aqueous layer to a final concentration of 2.5 M and the tubes placed overnight at −20° C.

The RNA was pelleted by centrifugation at 14,0000 rpm (4° C.) for 15 minutes; the pellet was washed with 1 ml of 70% ethanol (DEPC) and allowed to air dry for five minutes. The RNA was then suspended in 100 µl of DEPC water. The concentration and purity of RNA was determined by measuring the absorbance at 260 nm and 280 nm. The RNA was then diluted to give aliquots at a concentration of 200 ng/µl which were stored at −70° C.

Differential Display Analysis

All 3' anchoring and 5' arbitrary primers were obtained from the Genomyx Hieroglyph mRNA profile kit. The differential display procedure can be divided into three steps: cDNA synthesis, PCR amplification and gel electrophoresis.

First strand cDNA synthesis was carried using the Qiagen Omniscript reverse transcriptase.

A 20 µl reaction using one of the 12 Hieroglyph oligo (dT) anchored 3' primers and 400 ng of total RNA was used to generate enough cDNA for duplicated differential display PCR (DD-PCR) with the same oligo (dT) primer in pairwise combination with all four Hieroglyph arbitrary 5' primers.

2 µl of the 200 ng/µl RNA solution was added to a 0.2 ml thin-walled PCR tube along with 2 µl of Hieroglyph T7 (dT12) anchored primer (AP) (2 µM). This was then heated at 70° C. for five minutes before being placed on ice. To the denatured RNA/primer solution the following was added: 10xOmniscript reverse transcriptase (RT) buffer, 2 µl; 5 mM dNTP's, 2 µl; 0.1M DTT; 0.5 µl RNASEOUT RNase Inhibitor (40 µ/µl)(Gibco BRL); 1 µl Omniscript (1 unit/µl) and DEPC-water to 20 µl. The reaction mixtures were then incubated at 42° C. for 1 hour.

Differential Display PCR for each sample was then carried out in duplicate. DD-PCR reactions were performed using the Hieroglyph system (Genomyx), Clontech Taq polymerase mix, and [$\alpha$-$^{33}$P]dATP (3,000 Ci/mmole, Amersham).

For each cDNA sub-population, a PCR core mix containing the appropriate reverse transcriptase (RT) mix and matching anchored primers (AP) prepared in a volume sufficient for the number of reactions needed. The core mix included all the DD-PCR components with the exception of the arbitrary primers to be used, which were aliquoted separately into the appropriate tubes.

Each individual DD-PCR tube contained the components shown in Table 1.

TABLE 1

| DD-PCR component | [Stock] | 1× reaction Vo. (20 µl) | [Final] |
|---|---|---|---|
| Water | — | 9.35 µl | — |
| PCR Buffer | 10× | 2 µl | 1× |
| dNTP (1:1:1:1) | 250 µM | 2 µl | 20 µM |
| 5' ARP primer | 2 µM | 2 µl | 0.2 µM |
| 3' AP primer | 2 µM | 2 µl | 0.2 µM |
| cDNA | — | 2 µl | — |
| Taq | 50× | 0.4 µl | 1× |
| [$\alpha$-$^{33}$P]dATP | 10 µCi/µl | 0.25 µl | 0.125 µCi/µl |

Following DD-PCR, radiolabelled cDNA fragments were electrophoretically separated on a polyacrylamide gel under denaturing conditions. This involved using the Genomyx LR sequencer and LR-optimized HR-1000 polyacrylamide gel formulations. 4.5% and 6% HR-1000 gels were prepared according to manufacturers instructions; 4.5% gels were used to resolve fragments in the size range of 700 bp to 2 kb, while 6% gels were used to separate fragments in the size range of 100 bp to 600 bp.

7 μl or each DD-PCR sample was mixed with 4 μl of sample loading dye (Genomyx) and heated at 95° C. for 3 minutes before being chilled on ice. 3 μl of this heat-denatured sample was then added to a gel lane. Duplicate reactions were loaded in adjacent lanes and samples generated with the same primer pairs in consecutive lanes. 6% gels were used for 6 hours at 2,500 V, 100 W, at 50° C.; and 4.5% gels were used for 16 hours at 1,500 V, 100 W, at 50° C.

Following electrophoresis, the gel was dried on the glass plate in the Genomyx-LR sequencer according to the manufacturer's protocols. An autoradiograph of the gel was produced by placing a piece of BioMax MR (Kodak) ultra-high resolution film in contact with the gel, for 16 hours.

The autoradiograph showed bands corresponding to genes expressed in the non-repairing cells SVE 10 and MHP 15, but not expressed in the repairing cell lines MHP 36 and MHP 3. There were also bands corresponding to genes expressed in the repairing cell lines but not in the non-repairing cell lines.

Before excising bands from the gel, the autoradiograph was washed in 90% ethanol and allowed to dry. The autoradiograph was aligned on top of the gel with the aid of autorad markers (Stratgene). The autoradiograph was secured along one long edge with tape Differentially expressed transcripts (DET) were identified and the bands excised according to the Genomyx protocol. The excised bands were placed into 100 μl of elution buffer (EB, 10 mM Tris: HCl, pH 7.5) and the DNA allowed to elute at room temperature for six hours. The eluted DNA was stored at −20° C.

Single Strand Conformation Polymorphism (SSCP) gel analysis was used to eliminate false positives that may arise due to the co-migration of fragments of identical size but different sequences. This procedure involved a limited reamplification of the isolated fragments (SSCP-PCR) followed by the separation of the products of this amplification on a SSCP gel. PCR conditions were similar to those used for DD-PCR, with the exception that the number of cycles were reduced to 2 at the low annealing temperature (50° C.), and to 10 cycles at the high annealing temperature (60° C.). 4 μl of the SSCP-PCR reaction was added to 10 μl of SSCP-loading buffer (80% formamide, 0.01% bromophenol blue, 0.01% xylene cyanol, 1 mM EDTA, 10 mM NaOH) and denatured at 95° C. for 10 minutes before being loaded onto an agarose gel. Samples were electrophoresed for 16 hours at 8 W in 0.6 x tris borate EDTA buffer (TBE) on the Genomyx-LR sequencer. Following autoradiography, areas of the gel corresponding to candidate differentially expressed transcripts were excised and placed into 100 μl of elution buffer (EB).

Sequencing and Identification of DETs

The recovered differentially expressed cDNA was reamplified by PCR to provide significant template material to allow for direct sequencing. The PCR reactions contained the components shown in Table 2.

TABLE 2

| PCR component | [Stock] | 1× reaction Vo. (100 μl) | [Final] |
|---|---|---|---|
| Water | — | 49 μl | — |
| PCR Buffer | 10× | 10 μl | 1× |
| dNTP (1:1:1:1) | 250 μM | 10 μl | 20 μM |
| 5' ARP primer | 2 μM | 10 μl | 0.2 μM |
| 3' AP primer | 2 μM | 10 μl | 0.2 μM |
| SSCP-cDNA | — | 10 μl | — |
| Taq | 50× | 1 μl | 1× |

The PCR products were then purified using PCR purification kit (Qiagen), according to the manufacture's protocols. The purified products were eluted in 60 μl of elution buffer. Purified PCR products were sequenced using the Thermosequenase radiolabelled terminator cycle sequencing kit (Amersham). The reactions were performed using the M13 reverse primer (−48) (Genomyx) according to manufacturer's protocols. Sequencing products were loaded on to a 6% Long Ranger (FMC), 8 M Urea, 1 xGTB (glycerol-tolerant buffer) gel and electrophoresed for four hours at 2,500 V, 100 W, 50° C. in 1 xGTB. Following autoradiography, the sequencing ladders were read manually and the resulting sequence data was used to search the GenBank databases (both published and EST).

Table 3 shows the gene expression profile of the cell lines used in the experiment. MHP 36 and MHP 3 are cells that are suitable for transplantation into a damaged brain. It is clear that the expression profile in MHP36 and MHP3 is similar. Likewise, the profile in MHP15 and SVE10 is similar. However the profiles of MHP36/3 and MHP15/SVE10 are markedly different. This illustrates the difference in function of the two sets of cells as MHP15 and SVE10 cells do not have the ability to repair.

TABLE 3

| | Cell Line | | | | Homology | |
|---|---|---|---|---|---|---|
| DD-Band | MHP 3 | MHP 15 | MHP 36 | SVE 10 Clone23 | Gene | % |
| SEQ ID No. 1 A | +++++ | − | +++++ | − | Human EST | 88% over 68 bp |
| SEQ ID No. 2 B | +++++ | − | +++++ | − | Glogin-245 | 100% |
| SEQ ID No. 3 C | +++++ | − | +++++ | − | Mouse EST | 95% over 175 bp |
| SEQ ID No. 4 D | +++++ | − | +++++ | − | Mouse EST | 99% over 438 bp |
| SEQ ID No. 5 E | +++++ | − | +++++ | − | Heavy Chain immunoglob' | 94% over 108 bp |
| SEQ ID No. 6 F | − | +++++ | − | +++++ | Mouse EST | 91% over 84 bp |

TABLE 3-continued

| | Cell Line | | | | Homology | |
|---|---|---|---|---|---|---|
| DD-Band | MHP 3 | MHP 15 | MHP 36 | SVE 10 Clone23 | Gene | % |
| SEQ ID No. 7 G | – | +++++ | – | +++++ | Neuroprotective Protein, Adhp | 100% |

Analysis of the expression products revealed that the non-repairing MHP15 cells expressed a gene termed Pax6 (Gotz et al, Neuron (1998), 21;1031–1044), while cells from MPH36 did not express this gene.

Therefore, neural cells that express the Pax6 gene are not expected to be able to repair brain damage, while neural cell lines that do not express this gene are able to aid repair.

Pax6 is believed to be a positional specification gene, playing a role in determining the position an embryonic cell is fated to adopt in the developing brain (Fernandez et al, Development (1998) 125:2099–2111).

Further analysis revealed that the non-repairing, non-multipotential cells expressed the gene 3R3C (GeneBank Accession No. D25216). The MHP 36 cells did not express this gene when cultured under permissive conditions.

We claim:

1. A method for determining the suitability of a candidate cell for transplantation into a damaged vertebrate brain for the purpose of repairing damage to the brain, wherein said method comprises:
   (i) selecting a candidate cell with a neural cell phenotype, or which differentiates into a cell with a neural cell phenotype;
   (ii) obtaining the gene expression profile of said candidate cell;
   (iii) identifying a gene expression profile common to a plurality of control cells known to be suitable for transplantation, wherein the gene expression profile common to said plurality of control cells is selected from the group consisting of:
      (a) at least one expressed gene selected from the group consisting of SEQ ID NO. 1, SEQ ID NO. 2, SEQ ID NO. 3, SEQ ID NO. 4, and SEQ ID NO. 5;
      (b) at least one non-expressed gene selected from the group consisting of SEQ ID NO. 6 and SEQ ID NO. 7; and
      (c) at least one expressed gene selected from the group consisting of SEQ ID NO. 1, SEQ ID NO. 2, SEQ ID NO. 3, SEQ ID NO. 4, and SEQ ID NO. 5, and at least one non-expressed gene selected from the group consisting of SEQ ID NO. 6 and SEQ ID NO. 7;
   (iv) comparing the gene expression profile of said candidate cell with the gene expression profile common to said plurality of control cells; and
   (v) identifying said candidate cell as being suitable for transplantation if said candidate cell shares the gene expression profile of said plurality of control cells.

2. The method, according to claim 1, wherein the gene expression profile common to said plurality of control cells comprises at least one expressed gene selected from the group consisting of SEQ ID NO. 1, SEQ ID NO. 2, SEQ ID NO. 3, SEQ ID NO. 4, and SEQ ID NO. 5.

3. The method, according to claim 1, wherein the gene expression profile common to said plurality of control cells comprises at least one non-expressed gene selected from the group consisting of SEQ ID NO. 6 and SEQ ID NO. 7.

4. The method, according to claim 1, wherein the gene expression profile common to said plurality of control cells comprises at least one expressed gene selected from the group consisting of SEQ ID NO. 1, SEQ ID NO. 2, SEQ ID NO. 3, SEQ ID NO. 4, and SEQ ID NO. 5, and at least one non-expressed gene selected from the group consisting of SEQ ID NO. 6 and SEQ ID NO. 7.

5. The method, according to claim 1, wherein said plurality of control cells comprises an MHP36 cell and a different control cell.

6. The method, according to claim 1, wherein step (ii) is carried out by differential display.

7. The method, according to claim 1, wherein the gene expression profile common to said plurality of control cells comprises two or more expressed genes.

8. The method, according to claim 1, wherein said candidate cell is undifferentiated.

9. The method, according to claim 1, wherein said candidate cell is multipotent.

10. A method for identifying a gene, the expression of which can determine whether or not a neural cell can repair a damaged brain, wherein said method comprises:
    (i) selecting a candidate cell with a neural cell phenotype, or which differentiates into a cell with a neural cell phenotype;
    (ii) obtaining the gene expression profile of said candidate cell;
    (iii) identifying a gene expression profile common to a plurality of control cells known to be suitable for transplantation, wherein the gene expression profile common to said plurality of control cells is selected from the group consisting of:
       (a) at least one expressed gene selected from the group consisting of SEQ ID NO. 1, SEQ ID NO. 2, SEQ ID NO. 3, SEQ ID NO. 4, and SEQ ID NO. 5;
       (b) at least one non-expressed gene selected from the group consisting of SEQ ID NO. 6 and SEQ ID NO. 7; and
       (c) at least one expressed gene selected from the group consisting of SEQ ID NO. 1, SEQ ID NO. 2, SEQ ID NO. 3, SEQ ID NO. 4, and SEQ ID NO. 5, and at least one non-expressed gene selected from the group consisting of SEQ ID NO. 6 and SEQ ID NO. 7;
    (iv) comparing the gene expression profile of said candidate cell with the gene expression profile common to said plurality of control cells; and
    (v) identifying a gene within said gene expression profile of said candidate cell or within said gene expression profile common to said plurality of control cells, wherein said gene is expressed within said candidate cell but is not expressed within said plurality of control cells, or wherein said gene is not expressed within said candidate cell but is expressed within said plurality of control cells.

11. The method, according to claim 10, wherein the gene expression profile common to said plurality of control cells comprises at least one expressed gene selected from the group consisting of SEQ ID NO. 1, SEQ ID NO. 2, SEQ ID NO. 3, SEQ ID NO. 4, and SEQ ID NO. 5.

12. The method, according to claim 10, wherein the gene expression profile common to said plurality of control cells comprises at least one non-expressed gene selected from the group consisting of SEQ ID NO. 6 and SEQ ID NO. 7.

13. The method, according to claim 10, wherein the gene expression profile common to said plurality of control cells comprises at least one expressed gene selected from the group consisting of SEQ ID NO. 1, SEQ ID NO. 2, SEQ ID NO. 3, SEQ ID NO. 4, and SEQ ID NO. 5, and at least one non-expressed gene selected from the group consisting of SEQ ID NO. 6 and SEQ ID NO. 7.

14. The method, according to claim 10, wherein said plurality of control cells comprises an MHP36 cell and a different control cell.

15. The method, according to claim 10, wherein step (ii) is carried out by differential display.

16. The method, according to claim 10, wherein said candidate cell is undifferentiated.

17. The method, according to claim 10, wherein said candidate cell is multipotent.

* * * * *

```
                         SEQUENCE LISTING

<160> NUMBER OF SEQ ID NOS: 7

<210> SEQ ID NO 1
<211> LENGTH: 273
<212> TYPE: DNA
<213> ORGANISM: Mouse

<400> SEQUENCE: 1
gtggcctcaa  ccacattggt  actagtcaat  agcgcatgtg  gcttccctg   gacaacaagt      60 gagtttatgc  cctggaatgt  gtttgatggc  aagcttttcc  atcagaagta  ccgcagtctg     120
aaaagggata  tgccgtggaa  gttcttttgg  aacaaaatag  atcgtggctc  accaagttcc     180
acaacctgaa  ggcagtggtc  tgcaaggcct  gctccaagga  gaaccggcgc  atcgtaggca     240
gaacgcattg  ggactctcct  tacacaggga  ggc                                    273

<210> SEQ ID NO 2
<211> LENGTH: 325
<212> TYPE: DNA
<213> ORGANISM: Mouse

<400> SEQUENCE: 2
cataatttag  aagaccgttt  gaaaagatat  gaaaagaatg  catgtgcagc  aactgtgggg      60
acaccttaca  aaggtggcaa  tttgtaccac  actgaggtct  cactcttcgg  agaacctacc     120
gagtttgagt  atttgcgaga  agtgatgttt  gaatatatga  tgggtcgcga  gactaagacc     180
atggccaaag  ttataaccac  tgtcctgaaa  ttccctgatg  atcaggctca  gaaaattttg     240
gaaagagaag  atgctcgtct  gatgttgctt  ttctgttgat  tctgtgaaat  agactgatac     300
atggactaac  agccaccaag  aatgg                                              325

<210> SEQ ID NO 3
<211> LENGTH: 272
<212> TYPE: DNA
<213> ORGANISM: Mouse

<400> SEQUENCE: 3
ttgtagtggg  ctgccttcat  ccataggaag  tgtgtgtaaa  ttagatgaga  gcagtgctga      60
```

```
ggaggccgac aaatcgcgag aaagatctca gtgtgctgtg aaagctgcta ataaagattc      120
cagtgtcaca ccaaaaggga atttaagcaa tggaaacagt ggctctaaca gcaaagctgt      180
taaggaaaat gacaaagaaa aggcaaaga aaaagaaaaa aaagaaaaga ccccagctgt       240
tatccagagg ccgggtactt ggtaaagaca gt                                    272

<210> SEQ ID NO 4
<211> LENGTH: 438
<212> TYPE: DNA
<213> ORGANISM: Mouse

<400> SEQUENCE: 4
taccagttca agcactgccc atggttgtcc cacctcagga gcctgacaaa ccacctgcca      60
accttgctgc tactcttccc gttaggagta aagcagtcag tggaagagca tctgcaatgt      120
caaacactcc tacccacagt atcgctgctt ctgtttccca acctcagact ccaactccaa      180
gtcccatcat ctctccttca gccatgctac ctatctaccc tgccattgat attgatgcac      240
agactgagac taatcatgat actgcactaa cacttgcctg tgctggtggc catgaggaac      300
tggtacaaac actactagag agaggagcta gtattgaaca tcgagacaag aaaggtttta      360
ctggactcat cttggctgct acagctggtc atgttggtgt tgtagagata ttgctggaca      420
atggtgcaga cattgaag                                                    438

<210> SEQ ID NO 5
<211> LENGTH: 206
<212> TYPE: DNA
<213> ORGANISM: Mouse

<400> SEQUENCE: 5
gccatgtact actgtgccag acacacagtg tgggaagtcc aatgagagcc tgcacaaata      60
cttctctgca gggatgctca caaccagcag ggggcgctga ggacccaaag ggacttccca      120
ggatctcttc tggaatctag ggagctctga cctgtgtcta tcagcatgtg tttcaatgtt      180
agagttctta gttttccttc cagcaa                                           206

<210> SEQ ID NO 6
<211> LENGTH: 204
<212> TYPE: DNA
<213> ORGANISM: Mouse

<400> SEQUENCE: 6
aagtcacaat tactctgata cctaaaccac acaaagaccc aataagtaaa gagaacttca      60
gaccagtttc ccttatgaat atcaatgcaa aaaaagctca ataaaatttt cacaaaccga      120
agccaagaat aaaataaaag ccaagaataa aaggatcatc catcatgatc aagtaggctt      180
catcccaggg atgctgggat ggtt                                             204

<210> SEQ ID NO 7
<211> LENGTH: 267
<212> TYPE: DNA
<213> ORGANISM: Mouse

<400> SEQUENCE: 7
cgcgctttta aatgagaatg tctatagcgt tcacttcgaa aaggagcata aagctgagaa      60
agtcccagcc gtagctaact acattatgaa aatacacaat tttactagca aatgcctcta      120
```

-continued

```
ctgtaatcgc tatttgccta cagataccct acttcaacca tatgttaatt catggtctgt      180
cttgtccgta ttgccgttcc accttcaatg atgtagagaa gatggcagca cacatgcgaa      240
tggttcatat tgatgaagag atggggg                                          267
```